United States Patent

Ward

[11] 4,105,666
[45] Aug. 8, 1978

[54] PIPERIDINE DERIVATIVES

[75] Inventor: Terence James Ward, Slough, England

[73] Assignee: John Wyeth & Brother Limited, Maidenhead, England

[21] Appl. No.: 815,131

[22] Filed: Jul. 13, 1977

[30] Foreign Application Priority Data

Jul. 16, 1976 [GB] United Kingdom ............... 29419/76

[51] Int. Cl.² .......................................... C07D 211/58
[52] U.S. Cl. ................................ 260/293.77; 424/267
[58] Field of Search ...................... 260/293.77, 293.68, 260/293.67, 293.69

Primary Examiner—Norma S. Milestone

Attorney, Agent, or Firm—Arthur E. Wilfond

[57] ABSTRACT (Aroylamino)-1-(aroyloxyalkyl)piperidines having the formula

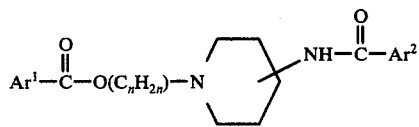

where $Ar^1$ and $Ar^2$ are aryl (including heteroaryl) groups and $n$ is from 2 to 6, and their pharmaceutically acceptable acid addition salts are described. The piperidine derivatives show hypotensive activity.

3 Claims, No Drawings

PIPERIDINE DERIVATIVES

This invention relates to piperidine derivatives a process for their preparation and pharmaceutical compositions containing them.

The invention provides novel piperidine derivatives having the formula I

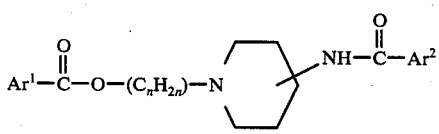

where $Ar^1$ and $Ar^2$ represent aryl radicals and $n$ denotes an integer of 2 to 6 and their pharmaceutically acceptable acid addition salts.

The aryl radicals represented by $Ar^1$ and $Ar^2$ may be the same or different. The term "aryl" as used herein includes both carbocyclic and heterocyclic aromatic radicals. Preferably, Ar and $Ar^1$ are independently selected from the group consisting of phenyl; phenyl substituted by one or two substituents selected from halogen, lower alkyl, lower alkoxy, nitro, trifluoromethyl and di(lower alkyl)amino; thienyl; furyl and pyridyl. As substituents for phenyl there may be mentioned, for example, methyl, ethyl, n-propyl, n-butyl, chlorine, bromine, methoxy, ethoxy, nitro, trifluoromethyl, dimethylamino and diethylamino, Advantageously the aryl radicals are unsubstituted phenyl. The term "lower" as used herein in connection with such groups as "alkyl" or "alkoxy" denotes that the group contains up to 6 carbon atoms, preferably up to 4 carbon atoms.

The divalent aliphatic hydrocarbon radical of the formula $-(C_nH_{2n})-$ is preferably a straight chain but may be branched. The symbol $n$ represents an integer from 2 to 6, preferably from 2 to 4. Illustrative examples of the divalent hydrocarbon radical include ethylene, trimethylene, propylene, tetramethylene and pentamethylene.

The aroylamino substituent having the formula $-NH-CO-Ar^2$ is preferably at the 4-position of the piperidine ring in formula I.

Examples of acid addition salts are those formed from inorganic and organic acids and in particular pharmaceutically acceptable acid addition salts such as the sulphate, hydrochloride, hydrobromide, hydroiodide, nitrate, phosphate, sulphonate (such as the methanesulphonate and p-toluenesulphonate), acetate, maleate, fumarate, tartrate, malonate, citrate and formate.

The invention also provides a process for the preparation of a piperidine derivative having the formula I

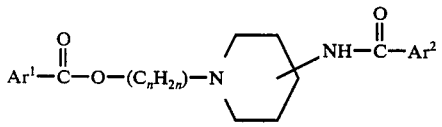

(wherein $Ar^1$, $Ar^2$ and $n$ are as defined above) or an acid addition salt thereof, wherein (a) an alcohol having the formula

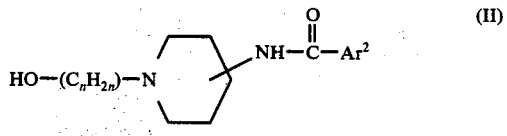

(where $Ar^2$ and $n$ are as defined above) or an acid addition salt thereof, is reacted with an acid having the formula $Ar^1COOH$ (where $Ar^1$ is as defined above) or a reactive derivative thereof, or (b) a compound having the formula

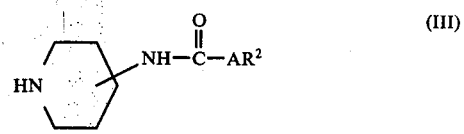

(where $Ar^2$ is as defined above) or an acid addition salt thereof is alkylated with an alkylating agent for introducing the substituted alkyl group having the formula

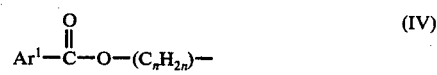

(where $Ar^1$ and $n$ are as defined above), or (c) a salt containing a cation having the formula V

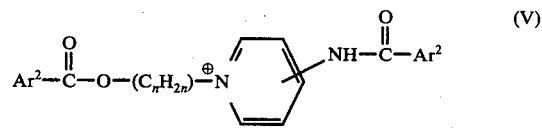

(wherein $Ar^1$, $Ar^2$ and $n$ are as defined above) is reduced to convert the pyridine ring to a piperidine ring, or (d) a compound having the formula VI

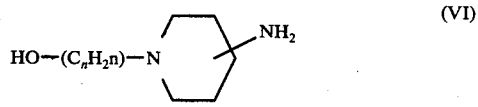

(where $n$ is as defined above) or an acid addition salt thereof is reacted with an acid having formula ArCOOH (where Ar is an aryl group) or a reactive derivative thereof, or (e) a compound having the formula VII

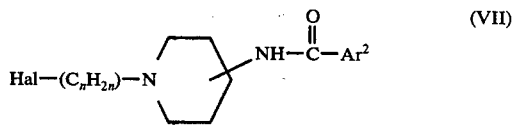

(where Hal is a halogen atom and $Ar^2$ and $n$ are as defined above) or an acid addition salt thereof is reacted with a suitable metal salt of an acid having formula $Ar^1COOH$ (where $Ar^1$ is as defined above), or (f) a compound having the formula VIII

(wherein Ar¹ and n are as defined above) or an acid addition salt thereof or an activated amino derivative thereof is reacted with an acid having the formula Ar²COOH (where Ar² and n are as defined above) or a reactive derivative thereof, and, if desired, a free base form of a compound having formula I is converted into an acid addition salt form or an acid addition salt form of compound having formula I is converted into the free base form.

Step (a) may be carried out by reaction of the alcohol of formula II or an acid addition with the acid of formula Ar¹COOH. The esterification may be carried out in known manner. The reaction is preferably carried out in the presence of a dehydrating agent or a small amount of an acid as catalyst, for example, hydrogen chloride or concentrated sulphuric acid. An excess of the aromatic acid of formula Ar¹COOH may be used. The water formed in the reaction is preferably removed from the reaction mixture, for example, by distillation.

Instead of using the acid having formula Ar¹COOH there may be used a reactive derivative of the acid, for example, an acid halide, particularly the acid chloride or acid bromide, or the acid anhydride. Step (a) may also be carried out by transesterification using an ester of the acid Ar¹COOH with a volatile alcohol, for example, the methyl or ethyl ester. The transesterification may be carried out with a suitable catalyst, for instance, hydrogen chloride or sulphuric acid. The volatile alcohol is distilled off from the reaction mixture.

The preferred method of carrying out step (a) consisting in reacting the alcohol of formula II or an acid addition salt thereof with the acid chloride of formula Ar¹COCl in the presence of a tertiary amine, for example, triethylamine.

The alcohols having formula II are generally known (see British patent specification No. 1,425,706). They may be prepared by reaction of a compound having the formula Hal—(C_nH_{2n})—OH (where n is as defined above and Hal is a halogen atom, preferably chlorine or bromine). The alcohols having formula II where HO—(C_nH_{2n})— is a β-hydroxyalkyl group may also be prepared by reaction of an epoxide such as ethylene oxide or propylene oxide with a compound having formula III.

Step (b) may be carried out in conventional manner for alkylation. In particular a compound having the formula IX

(where Ar¹ and n are as defined above and Hal is a halogen atom, preferably chlorine or bromine) may be reacted with the compound of formula III in the presence of a suitable acid acceptor, for example, an amine such as triethylamine.

Step (c) resides in the reduction of a pyridine derivative to form a piperidine derivative. The reaction may be carried out by catalytic hydrogenation, for instance, using a nickel catalyst. The compound having formula V may be prepared from an aminopyridine in known manner.

The ester formation of step (a) may also be combined with an acylation step to introduce the other aroyl radical in formula I. A single reagent may be used with the result that the two aroyl radicals, Ar¹CO— and Ar²CO—, are identical. Thus, for example, step (d) may be illustrated by reaction of a compound having the formula VI with an aroyl chloride in the presence of tertiary amine such as triethylamine to acylate both the amino and the hydroxyl functions of the compound having formula VI. The compound having formula VI may be prepared by alkylating a suitably protected amino piperidine to introduce the group HO—(C_nH_{2n})— at the piperidine nitrogen atom and removing the group protecting the amino substituent on the piperidine ring.

Step (e) is preferably carried out by reaction of the compound having formula VII with the silver salt of the acid of formula Ar¹COOH. The compound having formula VII may be prepared by reaction of a compound having formula II with a halogen-containing reagent that reacts with alcohols by replacing hydroxyl with halogen, for instance, thionyl chloride.

Step (f) may be carried out by reacting the acid having the formula Ar²COOH with the compound having formula VIII in the presence of a condensing agent, for instance, a carbodiimide. Alternatively the acid may be reacted with a derivative of the compound having formula VIII in which the amino function has been activated, for example, by forming the phosphazo derivative. The reactive acylating derivatives of the acid Ar²COOH may be employed for reaction with the compound having formula VIII. Examples of such acylating derivatives include the active esters, acyl halides, simple and mixed anhydrides and the acid azide. The acid halides, particularly the acid chloride, are especially suitable.

The compound having formula VIII may be prepared in known manner. In particular a compound having the formula

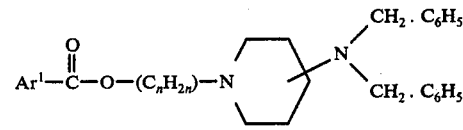

(where Ar¹ and n are as defined above) may be built up by known reactions and the two benzyl radicals used as protecting groups may be removed by hydrogenation.

Acid addition salts of the compound having formula I may be converted into the free base form in known manner by neutralisation with a base. The neutralisation conditions should be mild and the free base removed from the base without delay in order to prevent possible hydrolysis of the ester. The free base may itself be converted into an acid addition salt in standard manner, e.g. by adding ethereal or ethanolic hydrogen chloride to form the hydrochloride.

It will be appreciated that in the process of the invention it is expedient to avoid reaction conditions such as strong aqueous alkaline conditions which will hydrolyse the ester function of the compound having formula I.

The piperidine derivatives having formula I and their pharmaceutically acceptable acid addition salts are useful pharmaceutically. In particular they show hypotensive activity when tested on mammals according to standard procedure.

The following test procedure may be employed:

Charles River rats (200–250 g) are anaesthetised with pentobarbitone sodium (60 mg/kg i.p.). The animals are allowed to breathe spontaneously through tracheostomy tubes. Carotid arterial blood pressure is monitored and recorded. Drugs are administered via a catheter inserted in the jugular vein.

Control measurement of blood pressure and heart rate are taken immediately prior to and 30 seconds and 15 minutes following the injection of a dose of the test compound. The compound is administered over a cumulative dose range of 0.8–25.6 mg/kg i.v. The method is carried out in duplicate. Compounds are regarded as producing sustained hypotension if they produce a 30 mm Hg or more fall in diastolic blood pressure at 15 minutes. The compounds are regarded as showing transient hypotension if there is a 30 mm Hg or more fall at 30 seconds.

The compounds of Examples 1 and 2 produced sustained hypotension in this procedure at doses averaging about 14 mg/kg and 8 mg/kg respectively.

The invention also includes a pharmaceutical composition comprising a compound of formula I or a pharmaceutically acceptable salt thereof and a pharmaceutically acceptable carrier.

In the pharmaceutical compositions of the invention the active ingredient a compound of formula (1) as hereinbefore defined, may be micronised. In addition to the active ingredient, said compositions also contain a nontoxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. to 500 mg. according to the particular need and the activity of the active ingredient. The invention also includes the compounds in the absence of carrier where the compounds are in unit dosage form.

The following Examples illustrate the invention.

EXAMPLE 1

4-Benzamido-1-(2-benzoyloxyethyl)piperidine 1.4 Milliliters (0.012 mol) of benzoylchloride were added to a stirred solution of 2.48 grams (0.01 mol) of 4-benzamido-1-(2-hydroxyethyl)piperidine and 2.8 milliliters (0.02 mol) of triethylamine in 10 milliliters of dichloromethane. The solution was stirred at room temperature for 2 hours, then washed with water, dried and evaporated. The residue was crystallised from n-butyl acetate to give 2.5 grams (75% yield) of the title compound m.p. 139°–40° C. Treatment of a solution of the base in ethanol with ethanolic hydrogen chloride precipitated the hydrochloride, m.p. 217°–18° C.

Analysis: Found C, 64.34%; H, 6.59%; N, 7.05%. $C_{21}H_{25}ClN_2O_3 \cdot \frac{1}{2} H_2O$ requires C, 64.12%; H, 6.40: N, 7.12%.

EXAMPLE 2

4-Benzamido-1-(3-benzoyloxypropyl)piperidine

Treatment of 4-benzamido-1-(3-hydroxypropyl) piperidine with benzoyl chloride as in the previous example gave 3.4 grams (92.5% yield) of the title compound, m.p. 146°–7° C. Crystallisation from ethanolic hydrogen chloride afforded the hydrochloride, m.p. 211°–212° C.

Analysis: Found C, 65.59%; H, 6.87%; N, 7.08%. $C_{22}H_{27}ClN_2O_3$ requires C, 65.58%; H, 6.76; N, 6.95%.

EXAMPLE 3

Further products indicated below are obtained in a manner similar to Example 1 by using the acid chlorides and alcohols indicated.

| PRODUCT | ACID CHLORIDE | ALCOHOL |
|---|---|---|
| (a) 4-Benzamido-1-[3-(2-thienoyloxy)propyl] | 2-Thienoyl Chloride | 4-Benzamido-1-(3-hydroxypropyl)-pip- |

| PRODUCT | ACID CHLORIDE | ALCOHOL |
|---|---|---|
| piperidine | | eridine |
| (b) 4-Benzamido-1-[3-(2-furoyloxy)propyl]piperidine | 2-Furoyl Chloride | 4-benzamido-1-(3-hydroxypropyl)piperidine |
| (c) 4-Benzamido-1-[2-(3-pyridoyloxy)ethyl]piperidine | 3-Pyridoyl Chloride | 4-Benzamido-1-(2-hydroxyethyl)piperidine |
| (d) 1-[4-(p-Methoxybenzoyloxy)butyl]-4-(p-nitrobenzamido)piperidine | p-Methoxybenzoyl Chloride | 1-(4-Hydroxybutyl)-4-(p-nitrobenzamido)piperidine |
| (e) 4-(2,6-Dichlorobenzamido)-1-[3-(p-dimethylaminobenzoyloxy)propyl]piperidine | p-Dimethylaminobenzoyl Chloride | 4-(2,6-Dichlorobenzamido)-1-(3-hydroxypropyl)piperidine |
| (f) 4-(2-Methylbenzamido)-1-[2-(m-trifluoromethylbenzoyloxy)ethyl]piperidine | m-Trifluoromethylbenzoyl Chloride | 1-(2-Hydroxyethyl)-4-(2-methylbenzamido)piperidine |
| (g) 4-Benzamido-1-[3-(p-Bromobenzoyloxy)propyl]piperidine | p-Bromobenzoyl Chloride | 4-Benzamido-1-(3-hydroxypropyl)piperidine |
| (h) 4-Benzamido-1-[3-(p-toluoyloxy)propyl]piperidine | p-Toluoyl Chloride | 4-Benzamido-1-(3-hydroxypropyl)piperidine |

What is claimed is:

1. A compound selected from those having the formula I

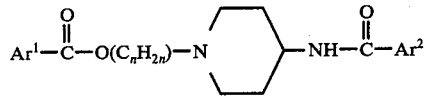

and their pharmaceutically acceptable acid addition salts, wherein $Ar^1$ and $Ar^2$ are independently selected from the group consisting of phenyl and phenyl substituted by one or two substituents selected from halogen, lower alkyl, lower alkoxy, nitro, trifluoromethyl and di(lower alkyl) amino; and $n$ represents an integer from 2 to 6.

2. A compound as claimed in claim 1, which is 4-benzamido-1-(2-benzoyloxyethyl)piperidine or a pharmaceutically acceptable acid addition salt thereof.

3. A compound as claimed in claim 1, which is 4-benzamido-1-(3-benzoyloxypropyl)piperidine or a pharmaceutically acceptable acid addition salt thereof.

* * * * *

UNITED STATES PATENT OFFICE
CERTIFICATE OF CORRECTION

PATENT NO. : 4,105,666
DATED : August 8, 1978
INVENTOR(S) : Terence J. Ward

It is certified that error appears in the above-identified patent and that said Letters Patent are hereby corrected as shown below:

Page 1, under Foreign Application Priority Data "Jul. 16, 1976 [GB] United Kindom ... 29419/76" should read -- Jul. 15, 1976 [GB] United Kingdom ... 29419/76 --.

Column 2, formula III, "AR$^2$" should read -- Ar$^2$ --.

Column 3, line 17, "addition with" should read -- addition salt thereof with --.

Column 6, line 34, "benzoylchloride" should read -- benzoyl chloride --.

Column 6, line 46, "H, 6.40" should read -- H, 6.40% --.

Column 6, line 58, "H, 6.76" should read -- H, 6.76% --.

Signed and Sealed this

Twenty-seventh Day of March 1979

[SEAL]

Attest:

RUTH C. MASON
Attesting Officer

DONALD W. BANNER
Commissioner of Patents and Trademarks